Jan. 23, 1968 H. C. SWIM ETAL Plant Pat. 2,792
ROSE PLANT
Filed July 20, 1966
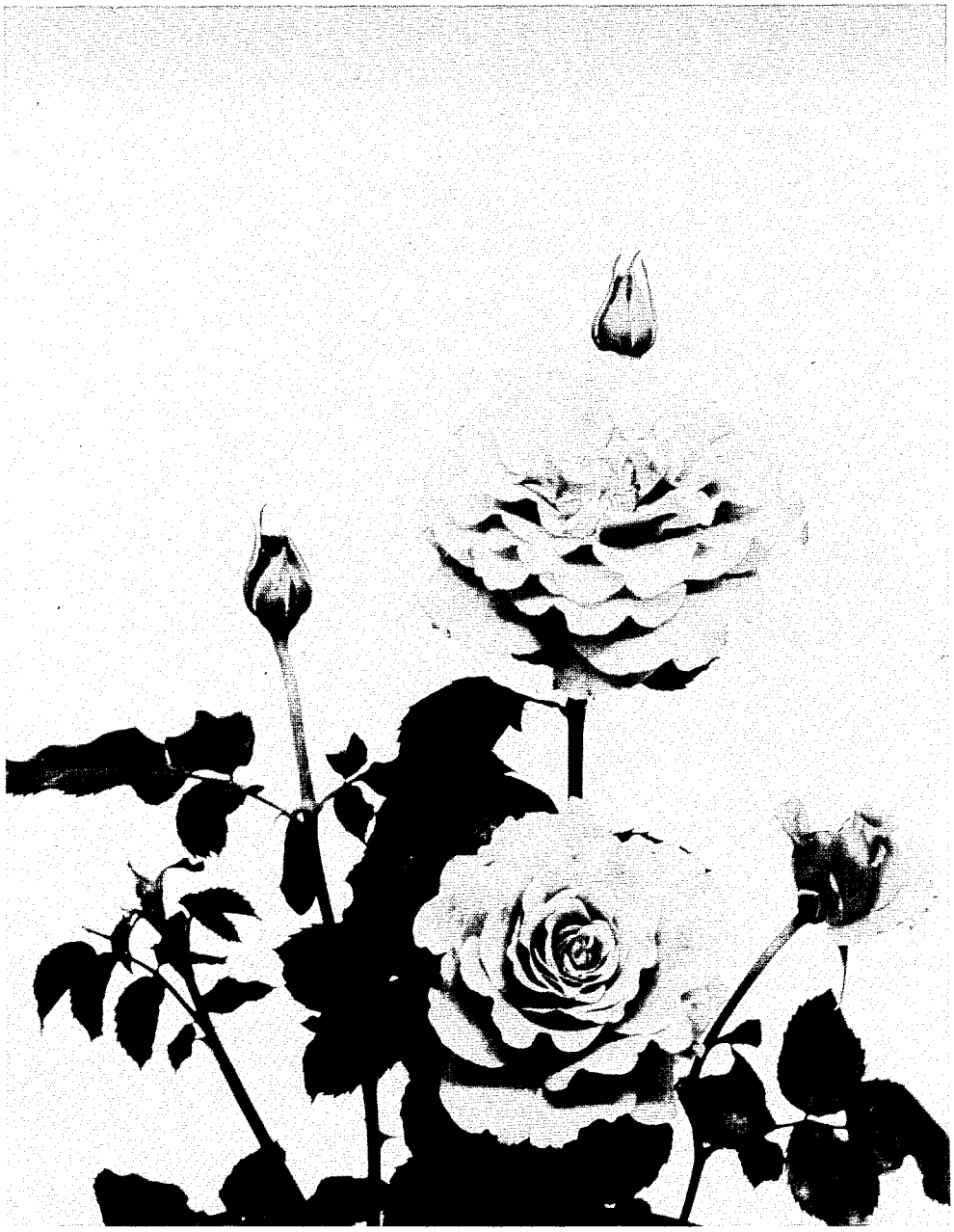
APPLICANTS
HERBERT C. SWIM
O. L. WEEKS
BY Synnestvedt & Lechner
ATTORNEYS United States Patent Office Plant Pat. 2,792

Patented Jan. 23, 1968

2,792

ROSE PLANT

Herbert C. Swim, Ontario, and O. L. Weeks, Chino, Calif., assignors, by mesne assignments, to The Conard-Pyle Company, West Grove, Pa., a corporation of Pennsylvania Filed July 20, 1966, Ser. No. 566,718
1 Claim. (Cl. Plt.—27)

The present invention relates to a new and distinct variety of rose plant which, when grown under greenhouse conditions, may be regarded as a hybrid tea rose, but which is functionally of the floribunda class when grown outdoors. The variety was originated by us by crossing an unnamed seedling (Circuit × Lavender Pinocchio) with the variety known as Sterling Silver (Plant Patent No. 1,433).

As a result of this breeding, we have produced a new and improved rose variety having the following unique characteristics which are outstanding therein, and which, taken together, distinguish it from its parents as well as from all other varieties of which we are aware:

(1) The color of the flower, which is deep mauve-lavender, as that term is popularly used;

(2) The strong and unique fragrance, much like that of ripe red raspberries;

(3) A characteristic waviness of the petals, which gives an attractive and unique look to the flower, from and after the time when it is about one-third open;

(4) The deep pigmentation of the new growth, which is reddish-purple in color;

(5) The high-centered form of the opening flower, the appearance of which calls to mind a coiled continuous line, unrolling;

(6) The high productivity of flowers which is nearly continuous when the plants are grown in a greenhouse; and (7) A warm rose-colored tone found in the open flowers, which is not usually found in the so-called lavender varieties.

The illustration which accompanies this application shows in natural colors outstanding characteristics of the plant and the development of the bloom from first bud to full-bloom maturity.

In comparison with the seed parent (Sterling Silver), the new variety:

(1) Has flowers of a mauve-lavender color, substantially deeper in shade than the lilac-colored flowers of the parent, and this color is uniform and fairly persistent, whereas the lighter color of the parent has a tendency to become still lighter after opening;

(2) The petals are waved or fluted in form, whereas the petals of Sterling Silver may be flat, or cupped, or serrated along the margins, but are never waved or fluted;

(3) The new growth is quite heavily pigmented with anthocyanin, whereas in Sterling Silver the anthocyanin pigmentation is only moderate.

The new variety is distinct from its pollen parent, an unnamed seedling which has not yet been introduced, and which resulted from the cross of Circuit × Lavender Pinocchio, in that:

(1) The flower color is a deep mauve-lavender, whereas the pollen parent would be described in popular terms as a medium lavender;

(2) The flowers are larger on the average than those of the pollen parent, ranging from three and seven-eighths to four and one-quarter inches in diameter, whereas the blooms of the pollen parent range from three and one-half to three and three-quarters inches;

(3) The mauve-lavender color of the new variety is fairly uniform in shade, and does not at any time show any of the brownish cast, reminiscent of Lavender Pinocchio, which is likely to be pronounced in the flowers of the pollen parent when they are from one-third to two-thirds open;

(4) The waved and fluted appearance of the fully opened flowers is quite different from the flat appearance of the pollen parent.

The new variety was asexually reproduced by budding, in the inventors' establishment at Chino, Calif. It has not yet been introduced to the trade. The new variety holds its distinguishing characteristics through succeeding propagations, and blooms more or less continuously during the season. In the greenhouse it may be classified as free blooming. The fragrance is quite strong, and unique, resembling that of ripe red raspberries. Flowers may be borne singly, or two or three may appear on a stem, the stems themselves being normal, strong and of medium length.

Details with respect to the plant and its bloom are as follows:

Bud: The peduncle is of medium length and medium caliper, normally erect, light green in color and almost smooth, while having a very few prickles and a moderate quantity of small stipitate glands.

Before the calyx breaks, buds are of medium size and short pointed form, sometimes with a conspicuous neck, and usually without foliaceous appendages on the surface; occasionally small foliacious appendages may extend beyond the tip of the bud, but usually this is not the case.

As the calyx breaks, its color is near Deep Purplish-Red, 10RP 3/10, on the Nickerson Color Fan, which is used throughout this specification to identify colors and shades which are not sufficiently indicated by their more common names.

As the petals first open, the bud is of medium size, and becomes urn-shaped in form. On the outside, its color at this time is near Brilliant Greenish-Yellow, 7.5Y 9/8 in a small broadly elliptical or fan-shaped area at the base (hereinafter termed, for convenience, the "lunula" by analogy to the white lunar segment at the base of a fingernail), changing rather abruptly to a color near Strong Purplish-Red, 7.5RP 5/12, which surrounds the lunula and merges about half way up into a color between Deep Purplish-Pink, 5RP 6/10, and Deep Purplish-Pink, 2.5RP 6/10, which extends to the top of the petal.

On the inside, the general color effect is that of a near Moderate Purplish-Red, 5RP 5/10, but the margins of the petals are somewhat lighter, near Moderate Purplish-Pink, 2.5RP 7/8. The bud opens up well.

Bloom: When fully open the bloom is of medium size, measuring from about three and seven-eighths inches to four and one-quarter inches. The petalage is double, but the stamens are not hidden. There may be from twenty-eight to thirty-two petals, arranged regularly, plus three or four petaloids. The bloom is high-centered in form at first, becoming ruffled in appearance at maturity. The petals are ruffled at first, and continue to be ruffled at maturity.

Petals: The petals are moderately thick and leathery, with inside shiny but crepe-like, while the outside is pebbled or crepe-like. The outer petals are broader than they are long in shape, with the apex often having many shallow notches. The intermediate petals are nearly round in flattened outline, are usually waved, and have one shallow notch in the apex. The inside petals are broadly obovate, and waved, usually having one notch in the apex.

The following description of a newly opened flower was made with reference to a rose grown in a greenhouse in March of 1966, at Chino, Calif.

The color of the outside petal, on its outer surface, was faintly yellow-white in the lunula, about the point of attachment to the base, merging rapidly into a color between Deep Purplish-Pink 5RP 6/10 and Deep Purplish-Pink 2.5RP 6/10, through the lower half of the petal. The remainder of the petal was near Moderate Purplish-Pink 2.5RP 7/8. As to the inside surface, the lunula was near Brilliant Greenish-Yellow 7.5Y 9/8 with a white vegetative streak extended from the base along the midrib about one-half the distance toward the apex on some of the petals. The remainder of the inside of the outer petals is between Deep Purplish-Pink 5RP 6/10 and Deep Purplish-Pink 2.5RP 6/10, the latter shade being dominant at the margins.

The outer surface of the intermediate petals was yellowish-white in the lunula. The remainder is fairly uniform in color, ranging between Moderate Purplish-Pink 2.5RP 7/8 and Moderate Purplish-Pink 10P 7/7. The inside surface of the intermediate petals was near Brilliant Greenish-Yellow 7.5Y 9/8 in the lunula. The remainder of the inner surface of the intermediate petals was fairly uniform in color, near Deep Purplish-Pink 2.5RP 6/10.

The inner petal has an outer surface which displays a yellowish-white lunula. An irregular white vegetative streak often follows the midrib to the apex. The remainder of the outer surface is between Moderate Purplish-Pink 2.5RP 7/8 and Moderate Purplish-Pink 10P 7/7. The inner surface of the inner petal has a lunula which is near Brilliant Greenish-Yellow 7.5Y 9/8. The remainder of the surface is fairly uniform in color, being near Deep Purplish-Pink 2.5RP 6/10.

The following description is made with respect to a rose that had been open for three days, in a greenhouse during the month of March, in the year 1966, at Chino, Calif.

The color of the outer surface of the outside petal is yellowish-white in the lunula. The remainder of the surface, except for a small border at the margins, is between Moderate Purplish-Pink 10P 7/7 and Light Purple 7.5P 7/7. The somewhat deeper tone near the margin is near Moderate Purplish-Pink 2.5RP 7/8. The inner surface of the outside petal likewise displays a small yellowish-white lunula, sometimes with a vegetative white streak which may follow the midrib for a short distance or radiate from the base parallel to the veins for a short ditsance. The remainder of the surface is somewhat mottled and varies between Deep Purplish-Pink 2.5RP 6/10 and Light Reddish-Purple 10P 6/9. The lunula of the outer surface of the inside petal is only faintly yellow-white. The remainder of the outer surface of the inside petal is of fairly uniform color, between Light Purple 7.5P 7/7 and Very Pale Purple 7.5P 8/5. The inner surface of the inside petal shows a yellowish-white lunula, the remainder of the surface being very slightly mottled, and varying between Moderate Purplish-Pink 10P 7/7 and Light Purple 7.5P 7/7.

The general color effect of the bloom as a whole lies between Deep Purplish-Pink 2.5RP 6/10 and Light Reddish Purple 10P 6/9 in the newly opened flower, whereas with the bloom which has been open for three days it appears as Moderate Purplish-Pink 10P 7/7 with a slightly deeper glow around the base of the petals.

The petals drop off cleanly, except for the petaloids, which tend to persist somewhat longer. Cut roses grown in the greenhouse, and kept at living room temperature, lasted for five days in the month of March, at Chino.

*Reproductive organs*

Stamens: Many (about 140) arranged fairly regularly about the pistils, some mixed with petaloids.

Filaments: Medium length, mostly white, some reddish, most with anthers.

Anthers: Medium size, light yellow, valves deep golden yellow; all opening very nearly at the same time.

Pollen: Abundant, golden yellow.

Pistils: Numerous—about 85.

Styles: Uneven, medium length, thin caliper, bunched, and somewhat columnar.

Stigma: Yellowish-white.

Ovaries: Mostly enclosed in, but some protruding from, the calyx.

Hips: Short, more or less flat, with some neck, yellow and russet in color, moderately smooth with thick fleshy walls.

Sepals: Persistent but not permanent, moderately short, spear-shaped to recurved.

Seeds: Many, of medium size.

*Plant*

Foliage: Compound leaves of three to five leaflets; normal in quantity and of medium to large size; moderately heavy, leathery and semi-glossy.

Leaflets are broadly ovate in shape, with apex acute to accuminate, base round to slightly cuneate, margin simply serrate, generally, but with some double serrations.

The leaf color at maturity is dark green on the upper surface and on the under surface shows, in addition, some reddish purple overlay in an irregular pattern. In the young foliage, the upper surface is very dark reddish purple, while the under surface is between Moderate Purplish Red 5RP 4/10 and Deep Purplish Red 7.5RP 3/9.

Rachis: Medium heavy weight, grooved, somewhat sparsely lined with stipitate glands on its upper side. On its under side it is smooth except for an occasional blunted prickle.

Stipules: Short and narrow, with short points recurved towards the stem.

When compared to about 100 other varieties grown under comparable conditions in a greenhouse at Chino, Calif., this new variety has about average to slightly better than average resistance to powdery mildew.

*Growth*

The plant is bushy in habit, ranging from upright to slightly spreading, and much branched. It is a free grower in the greenhouse.

The canes are of medium caliper. The main stems are dull olive green in color with from few to several large grey-brown prickles, these prickles being straight, of short to medium length, and with short to medium-width base. There are a few small prickles, and these are of a grey-brown color. There are no hairs. The branches are dull olive green with some reddish purple overlay, bearing from few to several large prickles of medium length and with medium-long oval base. The color of the large prickles varies from reddish purple at the base to greenish yellow at the tips. There are a few small prickles of reddish purple color on the branches, but no hairs. The new shoots are reddish purple, carrying a few medium length large prickles which are straight, with short oval base, their color being reddish purple to a varying degree. The new growth has relatively few small prickles which are reddish purple in color. It has no hairs.

We claim:

1. The new variety of hybrid tea rose herein shown and described, which is characterized; as to its flower, by an initially high-centered form, and later by the wavy appearance imparted by its fluted petals, and the unrolling-line pattern which they form as they open; by its deep mauve-lavender color; and by its strong and unique fragrance; the plant itself being characterized by the deep pigmentation of the new growth, and by its nearly continuous productivity of flowers under greenhouse conditions.

No references cited.

ROBERT E. BAGWILL, *Primary Examiner.*

UNITED STATES PATENT OFFICE

CERTIFICATE OF CORRECTION

Plant Patent No. 2,792 January 23, 1968

Herbert C. Swim et al.

It is hereby certified that error appears in the above numbered patent requiring correction and that the said Letters Patent should read as corrected below.

Column 1, lines 14 and 60, for "Circuit", each occurrence, read -- circus --; column 3, line 45, for "ditsance" read -- distance --.

Signed and sealed this 22nd day of April 1969.

(SEAL)
Attest:

Edward M. Fletcher, Jr.
Attesting Officer

EDWARD J. BRENNER
Commissioner of Patents